United States Patent
Yan et al.

(10) Patent No.: US 9,012,666 B2
(45) Date of Patent: Apr. 21, 2015

(54) METHOD FOR PRODUCING 30-HALOGENATED BETULINIC ACID

(75) Inventors: Xiufeng Yan, Zhejiang (CN); Mingjiang Wu, Zhejiang (CN); Lihua Wang, Zhejiang (CN); Ping Yu, Zhejiang (CN); Nan Li, Zhejiang (CN)

(73) Assignee: Wenzhou University, Zhejiang (CN)

( * ) Notice: Subject to any disclaimer, the term of this patent is extended or adjusted under 35 U.S.C. 154(b) by 0 days.

(21) Appl. No.: 14/355,427

(22) PCT Filed: Mar. 15, 2012

(86) PCT No.: PCT/CN2012/072375
§ 371 (c)(1),
(2), (4) Date: Apr. 30, 2014

(87) PCT Pub. No.: WO2013/071722
PCT Pub. Date: May 23, 2013

(65) Prior Publication Data
US 2014/0296546 A1    Oct. 2, 2014

(30) Foreign Application Priority Data
Nov. 18, 2011   (CN) .......................... 2011 1 0366870

(51) Int. Cl.
*C07J 53/00* (2006.01)
*C07J 63/00* (2006.01)

(52) U.S. Cl.
CPC ............... *C07J 53/002* (2013.01); *C07J 63/00* (2013.01)

(58) Field of Classification Search
CPC ...... C07C 2103/52; C07C 29/62; C07C 51/29
See application file for complete search history.

(56) References Cited

U.S. PATENT DOCUMENTS 5,468,888 A * 11/1995 Bouboutou et al. ............ 554/58

FOREIGN PATENT DOCUMENTS

WO   WO 2008/070347 A2 * 11/1995
WO   2008127364        10/2008

OTHER PUBLICATIONS

Zaragoza Dorwald (Side Reactions in Organic Synthesis, 2005, WILEY-VCH Verlag GmbH & Co. KGaA, Weinheim, Preface. Pg. IX.*
Barthel et al, Tetrahedron, Oxidative Transformations of Betulinol, 2008, 64, pp. 9225-9229.*
Tang Jun etal., "Selective oxidation of betulin for betulinic acid preparation", Journal of Dalian Polytechnic University, Jul. 2009, vol. 28, No. 4, pp. 244-247.
Zhu Wei, "Application technology and development of dibromohydantoin", China New Technologies and Products, Feb. 2011, No. 2, p. 150 (abstract translated with Google translate).
Zhong Ping etal., "Synthesis and application of trichloroiminocyanuric acid", Chemical Reagents, 2003, vol. 25, No. 1, pp. 15-17.

* cited by examiner

*Primary Examiner* — Paul A Zucker
(74) *Attorney, Agent, or Firm* — Vidas, Arrett & Steinkraus

(57) ABSTRACT

The invention discloses a method for producing 30-halogenated betulinic acid. Betulin is used as a raw material and selectively oxidized and halogenated to generate 30-betulinic acid, and the selected oxidation and halogenation agent has high selectivity and does not affect C-3 hydroxyl or carbon-carbon double bonds. Oxidation and halogenation are completed in one step, so the process route is short, the treatment method is simple, and the product is purified easily.

6 Claims, No Drawings

METHOD FOR PRODUCING 30-HALOGENATED BETULINIC ACID

CROSS-REFERENCE TO RELATED APPLICATIONS

This application claims the benefit of PCT Application No. PCT/CN2012/072375, filed Mar. 15, 2012, which claims priority to Chinese Patent Application No. 201110366870.7, filed Nov. 18, 2011, the entire content of each of which are hereby incorporated herein by reference.

TECHNICAL FIELD OF THE INVENTION

The present invention relates to the preparation of derivatives of natural compounds, and more particularly to a method of semi-synthesis of 30-halogenated betulinic acid from betulinol.

BACKGROUND

Betulinic acid (II) and betulinol (also known as betulin, III) are plant secondary metabolites of pentacyclic triterpenoids. The bark of silver birch has a high betulinol content which can reach 10 to 35%, and betulinic acid can be obtained from semi-synthesis of betulinol. Betulinic acid has biological activities of anti-malarial, anti-inflammatory and anti-HIV, and shows cytotoxic activity against a number of tumor cell lines, which is a promising precursor compound for application and development of anti-cancer and anti-AIDS drugs. Betulinic acid derivatives with excellent biological activities has been obtained by structural modifications to betulinic acid as a precursor compound. According to the structural characteristics of betulinic acid, it is mainly focused on the chemical modification sites at C-3, C-19 and C-28, and 30-halogenated betulinic acid (I) is an important intermediate for C-19 modification (N. V. Uzenkova et al., Bioorganic & Medicinal Chemistry Letters, 2005, 41:692; J. Y. Kim et al., Chemistry of Natural Compounds. 2001, 11:2405).

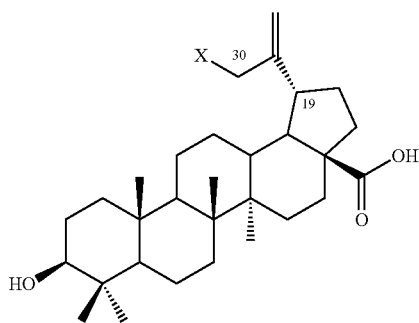

I

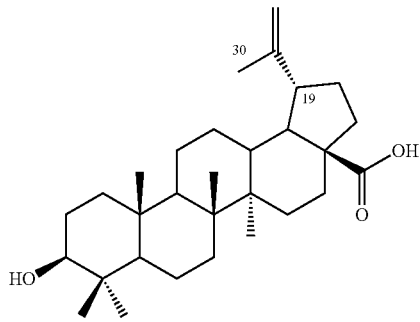

II

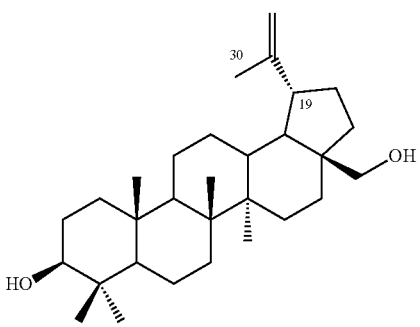

III

The synthesis of 30-brominated betulinic acid has been reported. In 1976, Achari et al. (Tetrahedron, 1976, 32(6): 741) published a paper entitled "Studies on Indian medicinal plants. XXXIX. Reinvestigation of the lactones and bromo derivative of betulinic acid". In this method, 30-bromo betulinic acid is prepared by using betulinic acid as starting material, comprising protection of C-3 hydroxyl and C-28 carboxyl groups, subsequent C-30 bromination reaction and final deprotection. In 2008, a PCT patent entitled "Preparation of betulinic acid derivatives for use in antiviral and anticancer pharmaceutical compositions" was published (WO2008127364), which provides a method for preparing 30-bromo betulinic acid by using betulinic acid as starting material. Both the methods using betulinic acid as starting material are not suitable for large-scale production due to high production cost.

BRIEF SUMMARY OF THE INVENTION

An object of the present invention is to provide a method for directly producing 30-halogenated betulinic acid by selective oxidation and halogenation of betulinol with advantages of simple process route and easy purification of the product.

To achieve the above object, the present invention provides a process route in that betulinol is directly and selectively oxidized and halogenated to generate a crude 30-halogenated betulinic acid and then the crude is purified to obtain 30-halogenated betulinic acid.

In the method, the 30-halogenated betulinic acid can be selected from 30-chloro-betulinic acid and 30-bromo-betulinic acid.

In particular, the method for producing 30-halogenated betulinic acid uses betulinol as starting material, comprising the following steps in turn:

(1) Oxidation and halogenation of betulinol to prepare a crude 30-halogenated betulinic acid: betulinol being dissolved in an organic solvent and added with 2,2,6,6-tetramethyl-1-piperidone, sodium bicarbonate and an oxidizing and halogenating agent and stirred at 40~60° C. for 3~5 hours; then the reaction being terminated by adding ethanol, filtered, and the filtrate being acidified with hydrochloric acid to pH of 3.5 to 4.5, concentrated under reduced pressure to precipitate out, and then the resulting precipitate being filtered and washed with distilled water and naturally dried to generate a crude 30-halogenated betulinic acid.

(2) Purification of the crude 30-halogenated betulinic acid to obtain 30-halogenated betulinic acid product: the crude 30-halogenated betulinic acid being purified by recrystallization to obtain 30-halogenated betulinic acid product.

The advantages of the present invention comprise:

1. 30-halogenated betulinic acid is prepared by selective oxidation and halogenation of betulinol as starting material without any protection of functional groups due to the high selectivity of the selected oxidizing and halogenating agent.
2. The oxidation and halogenation reactions are effected in one step, so as to achieve short process route, simple treatment process and easy product purification.

DESCRIPTION OF THE PREFERRED EMBODIMENTS

The present invention is further described in combination of the following examples in details.

A method for producing 30-halogenated betulinic acid in that betulinol is selectively oxidized and halogenated to generate a crude 30-halogenated betulinic acid, and then the crude is purified to obtain 30-halogenated betulinic acid product.

In the method for producing 30-halogenated betulinic acid, the 30-halogenated betulinic acid can be selected from 30-chloro-betulinic acid and 30-bromo-betulinic acid.

In particular, the method for producing 30-halogenated betulinic acid uses betulinol as starting material, comprising the following sequential steps:

(1) Oxidation and halogenation of betulinol to prepare a crude 30-halogenated betulinic acid: the betulinol being dissolved in an organic solvent and added with 2,2,6,6-tetramethylpiperidine 1-oxyl, sodium bicarbonate and an oxidizing and halogenating agent, and stirred at 40~60° C. for 3~5 hours, then the reaction being terminated by adding ethanol, filtered, and the filtrate being acidified with hydrochloric acid to pH of 3.5 to 4.5, concentrated under reduced pressure to precipitate out, and then the resulting precipitate being filtered and washed with distilled water and naturally dried to generate a crude 30-halogenated betulinic acid.

(2) Purification of the crude 30-halogenated betulinic acid to obtain 30-halogenated betulinic acid product: the crude 30-halogenated betulinic acid being purified by recrystallization to obtain 30-halogenated betulinic acid product.

In the step (1), the molar ratio of the betulinol to the 2,2,6,6-tetramethylpiperidine 1-oxyl is from 1:0.2 to 1:0.3, and the molar ratio of the betulinol to the sodium bicarbonate is from 1:2 to 1:5, and the molar ratio of the betulinol to the oxidizing and halogenating agent is from 1:1 to 1:3.5, and the amount of the organic solvent is from 100 to 200 ml/g of betulinol.

In the step (1), the organic solvent is selected from ethyl acetate and ethyl butyrate.

In the step (1), the oxidizing and halogenating agent is selected from trichloroisocyanuric acid, N-chlorosuccinimide, 1,3-dibromo-5,5-dimethylhydantoin and N-bromo-phthalimide.

In the step (2), the recrystallization solvent is selected from methanol and ethanol, and the recrystallization is repeated 2 or 3 times.

EXAMPLE 1

44.3 g (0.1 mol) of betulinol were dissolved in 4430 ml of ethyl acetate, added with 3.12 g (0.02 mol) of 2,2,6,6-tetramethylpiperidine 1-oxyl, 25.2 g (0.3 mol) of sodium bicarbonate and 46.7 g (0.35 mol) of N-chlorosuccinimide under stirring in turn, after reacted at 60° C. for 5 hours under stirring, the reaction was terminated by adding 10 ml of ethanol, and then the reaction product was filtered, and the filtrate was acidified by dropwise adding dilute hydrochloric acid to pH 3.5, concentrated under reduced pressure to precipitated out, and then the resulting precipitate was filtered and washed with distilled water, then naturally dried to give 47.3 g of crude 30-chloro-betulinic acid. The resulting crude 30-chloro betulinic acid was recrystallized twice from methanol to obtain 30-chloro betulinic acid product (40.8 g, purity 95.6%, and yield 79.3%).

EXAMPLE 2

44.3 g (0.1 mol) of betulinol were dissolved in 8860 ml of ethyl butyrate, added with 4.68 g (0.03 mol) of 2,2,6,6-tetramethylpiperidine 1-oxyl, 42.0 g (0.5 mol) of sodium bicarbonate and 42.9 g (0.15 mol) of 1,3-dibromo-5,5-dimethylhydantoin under stirring in turn, after reacted at 40° C. for 3 hours under stirring, the reaction was terminated by adding 10 ml of ethanol, and then the reaction product was filtered, and the filtrate was acidified by dropwise adding dilute hydrochloric acid to pH 4.5, concentrated under reduced pressure to precipitated out, and then the resulting precipitate was filtered and washed with distilled water, then naturally dried to give 52.6 g of crude 30-chloro-betulinic acid. The resulting crude 30-chloro betulinic acid was recrystallized three times from ethanol to obtain 30-chloro betulinic acid product (38.8 g, purity 97.1%, and yield 70.3%).

EXAMPLE 3

44.3 g (0.1 mol) of betulinol were dissolved in 6500 ml of ethyl acetate, added with 4.68 g (0.03 mol) of 2,2,6,6-tetramethylpiperidine 1-oxyl, 42.0 g (0.5 mol) of sodium bicarbonate and 23.2 g (0.1 mol) of trichloroisocyanuric acid under stirring in turn, after reacted at 50° C. for 3 hours under stirring, the reaction was terminated by adding 10 ml of ethanol, and then the reaction product was filtered, and the filtrate was acidified by dropwise adding dilute hydrochloric acid to pH 4.5, concentrated under reduced pressure to precipitated out, and then the resulting precipitate was filtered and washed with distilled water, then naturally dried to give 48.6 g of crude 30-chloro-betulinic acid. The resulting crude 30-chloro betulinic acid was recrystallized three times from methanol to obtain 30-chloro betulinic acid product (40.1 g, purity 98.1%, and yield 80.1%).

EXAMPLE 4

44.3 g (0.1 mol) of betulinol were dissolved in 8000 ml of ethyl butyrate, added with 4.68 g (0.03 mol) of 2,2,6,6-tetramethylpiperidine 1-oxyl, 33.6 g (0.4 mol) of sodium bicarbonate and 67.5 g (0.3 mol) of N-bromo-phthalimide under stirring in turn, after reacted at 60° C. for 5 hours under stirring, the reaction was terminated by adding 10 ml of ethanol, and then the reaction product was filtered, and the filtrate was acidified by dropwise adding dilute hydrochloric acid to pH 4.5, concentrated under reduced pressure to precipitated out, and then the resulting precipitate was filtered and washed with distilled water, then naturally dried to give 48.6 g of crude 30-chloro-betulinic acid. The resulting crude 30-chloro betulinic acid was recrystallized three times from ethanol to obtain 30-chloro betulinic acid product (37.8 g, purity 95.1%, and yield 77.0%).

To be claimed:

1. A method for producing 30-halogenated betulinic acid, wherein betulinol as a raw material is selectively oxidized and halogenated to give directly a crude 30-halogenated betulinic acid in one step by using an oxidizing and halogenating agent selected from trichloroisocyanuric acid, N-chlorosuccinimide, 1,3-dibromo-5,5-dimethylhydantoin and N-bromo-phthalimide, and then the crude 30-halogenated betulinic acid is purified to obtain 30-halogenated betulinic acid product.

2. The method for producing 30-halogenated betulinic acid according to claim 1, wherein the 30-halogenated betulinic acid is selected from 30-chloro-betulinic acid and 30-bromo-betulinic acid.

3. The method for producing 30-halogenated betulinic acid according to claim 1, wherein betulinol is used as starting material, comprising the following steps in turn:

(1) Oxidation and halogenation of betulinol to prepare a crude 30-halogenated betulinic acid: the betulinol being dissolved in an organic solvent and added with 2,2,6,6-tetramethylpiperidine 1-oxyl, sodium bicarbonate and an oxidizing and halogenating agent, stirred at 40~60° C. for 3~5 hours, then terminating the reaction by adding ethanol, filtering, and the filtrate being acidified with hydrochloric acid to pH of 3.5 to 4.5, concentrated under reduced pressure to precipitate out, and then the resulting precipitate being filtered and washed with distilled water and naturally dried to give a crude 30-halogenated betulinic acid; and (2) Purification of the crude 30-halogenated betulinic acid to obtain 30-halogenated betulinic acid product: the crude 30-halogenated betulinic acid being purified by recrystallization to obtain 30-halogenated betulinic acid product.

4. The method for producing 30-halogenated betulinic acid according to claim 3, wherein in the step (1), the molar ratio of the betulinol to the 2,2,6,6-tetramethylpiperidine 1-oxyl is from 1:0.2 to 1:0.3, and the molar ratio of the betulinol to the sodium bicarbonate is from 1:2 to 1:5, and the molar ratio of the betulinol to the oxidizing and halogenating agent is from 1:1 to 1:3.5, and the amount of the organic solvent is from 100 to 200 ml/g of betulinol.

5. The method for producing 30-halogenated betulinic acid according to claim 3, wherein in the step (1), the organic solvent is selected from ethyl acetate and ethyl butyrate.

6. The method for producing 30-halogenated betulinic acid according to claim 3, wherein in the step (2), the recrystallization solvent is selected from methanol or ethanol, and the recrystallization is repeated 2 or 3 times.

* * * * *